(12) United States Patent
Baets et al.

(10) Patent No.: US 8,772,440 B2
(45) Date of Patent: Jul. 8, 2014

(54) PROCESS FOR MANUFACTURING LACTIC ACID

(75) Inventors: Peter Johannes Marie Baets, Spijk (NL); Willem Jacob Groot, Dordrecht (NL)

(73) Assignee: Purac Biochem B.V., Gorichem (NL)

( * ) Notice: Subject to any disclaimer, the term of this patent is extended or adjusted under 35 U.S.C. 154(b) by 0 days.

(21) Appl. No.: 13/577,398

(22) PCT Filed: Feb. 8, 2011

(86) PCT No.: PCT/EP2011/051791
§ 371 (c)(1),
(2), (4) Date: Oct. 4, 2012

(87) PCT Pub. No.: WO2011/095631
PCT Pub. Date: Aug. 11, 2011

(65) Prior Publication Data
US 2013/0225787 A1  Aug. 29, 2013

Related U.S. Application Data

(60) Provisional application No. 61/302,372, filed on Feb. 8, 2010.

(30) Foreign Application Priority Data

Feb. 8, 2010  (EP) ..................... 10152963

(51) Int. Cl.
*C08G 64/00* (2006.01)
*C08G 63/02* (2006.01)

(52) U.S. Cl.
USPC ...................................................... 528/361

(58) Field of Classification Search
USPC ...................................................... 528/361
See application file for complete search history.

(56) References Cited

U.S. PATENT DOCUMENTS

| | | | |
|---|---|---|---|
| 5,258,488 A | 11/1993 | Gruber | |
| 5,766,439 A | 6/1998 | Eyal | |
| 7,705,180 B2 * | 4/2010 | van Krieken et al. | ......... 562/589 |
| 2004/0116740 A1 | 6/2004 | Van Krieken | |

FOREIGN PATENT DOCUMENTS

| | | |
|---|---|---|
| CN | 1270953 | 10/2000 |
| EP | 0393818 | 2/1990 |
| WO | WO 96/41021 | 12/1996 |
| WO | WO 98/37050 | 8/1998 |
| WO | WO 99/19290 | 4/1999 |
| WO | WO 01/38283 | 5/2001 |
| WO | WO 2005/123647 | 12/2005 |

OTHER PUBLICATIONS

European Search Report and Written Opinion of the European Patent Office Patent Office in counterpart foreign application No. PCT/EP2011/051791 filed Feb. 8, 2011.

Eun Gyo Lee, et al., "Lactic acid recovery using two-stage electrodialysis and its modelling," Journal of Membrane Science, vol. 145, pp. 53-66, 1998 (14 pages).

* cited by examiner

*Primary Examiner* — Terressa Boykin
(74) *Attorney, Agent, or Firm* — Peter J. Ims; Westman, Champlin & Koehler, P.A.

(57) ABSTRACT

A process for the preparation of lactic acid includes:
a) providing an aqueous medium comprising magnesium lactate;
b) adding to the aqueous medium a monovalent base to form an aqueous medium comprising a water soluble monovalent lactate salt and a solid magnesium base;
c) separating the magnesium base from the aqueous medium;
d) adjusting the concentration of the monovalent lactate salt in the aqueous medium,
e) subjecting the aqueous medium to water-splitting electrodialysis, to produce a first solution comprising monovalent base and a second solution comprising lactic acid and monovalent lactate salt, the electrodialysis being carried out to a partial conversion of 40 to 98 mole %;
f) separating the second solution into lactic acid and a solution comprising the monovalent lactate salt by vapour-liquid separation;
g) recycling the solution of step f) comprising the monovalent lactate salt to step d).

23 Claims, No Drawings

PROCESS FOR MANUFACTURING LACTIC ACID

CROSS-REFERENCE TO RELATED APPLICATION

This Application is a Section 371 National Stage Application of International Application No. PCT/EP2011/051791, filed Feb. 8, 2011 and published as WO 2011/095631 on Aug. 11, 2011, in English, which in turn is based on and claims benefit of U.S. Provisional Application No. 61/302,372, filed Feb. 8, 2010.

BACKGROUND

The discussion below is merely provided for general background information and is not intended to be used as an aid in determining the scope of the claimed subject matter.

An aspect of the present invention pertains to a process for manufacturing lactic acid in high purity in an economical manner.

Lactic acid is often manufactured via fermentation of carbohydrates by micro-organisms. A common feature to all fermentation processes is the need to neutralise the acids excreted by the micro-organisms. A drop in pH below a critical value, depending on the micro-organism used in the process, could damage the micro-organism's metabolic process and bring the fermentation process to a stop. Therefore, it is common practice to add a base in the fermentation media in order to control the pH. This results in the lactic acid produced being present in the fermentation media in the form of a lactate salt.

Despite the longstanding practice to produce lactic acid via fermentation, one of the challenges in the manufacture of lactic acid is still to obtain the acid in a relatively pure form while at the same time carrying out the process in an economical manner on a scale which is commercially attractive.

Electrodialysis is one of the purification processes that may be used in the production of lactic acid via fermentation. Water-splitting electrodialysis in particular allows the direct conversion of the lactate salt into lactic acid and base. In this type of electrodialysis bipolar membranes are generally used to split water into $H^+$ and $OH^-$ respectively, which combine with the anion and cation of the lactate salt respectively, resulting in the production of separate solutions of lactic acid and base.

The use of water-splitting electrodialysis on aqueous media provided by fermentation, in particular for manufacturing organic acids, has been limited by the necessity to remove fermentation-derived products from the feed (e.g. sugar, protein and amino acids). Such fermentation derived matter negatively interferes with the water-splitting electrodialysis process by, for instance, fouling of the ion-permeable membranes and increasing the power consumption.

There is still need for a process for manufacturing lactic acid which provides lactic acid in high purity and which can be performed in an economical manner with low power consumption, without producing substantial amounts of non-reusable components (i.e. waste by-products) and without substantial yield loss.

SUMMARY

This Summary and the Abstract herein are provided to introduce a selection of concepts in a simplified form that are further described below in the Detailed Description. This Summary and the Abstract are not intended to identify key features or essential features of the claimed subject matter, nor are they intended to be used as an aid in determining the scope of the claimed subject matter. The claimed subject matter is not limited to implementations that solve any or all disadvantages noted in the Background.

An aspect of the present disclosure includes a process where lactate, preferably magnesium lactate provided by fermentation, is treated by means of salt exchange to provide an aqueous solution of a monovalent lactate salt which is especially suited for water-splitting electrodialysis. Lactic acid of high purity is then produced by using water-splitting electrodialysis with partial conversion of lactate to the acid, separating the lactic acid from the lactate salt by vapour-liquid separation and recycling the lactate salt to the electrodialysis process.

DETAILED DESCRIPTION

Accordingly, an aspect of the present invention pertains to a process for the preparation of lactic acid comprising the steps of:

a) providing an aqueous medium comprising magnesium lactate;
b) adding to the aqueous medium comprising magnesium lactate a monovalent base to form an aqueous medium comprising a water soluble monovalent lactate salt and a solid magnesium base;
c) separating the solid magnesium base from the aqueous medium comprising the water soluble monovalent lactate salt;
d) adjusting the concentration of the monovalent lactate salt in the aqueous medium to a value between 10 and 30 wt. %;
e) subjecting the aqueous medium comprising the monovalent lactate salt to water-splitting electrodialysis, to produce a first solution comprising monovalent base and a second solution comprising lactic acid and monovalent lactate salt, the electrodialysis being carried out to a partial conversion of 40 to 98 mole %;
f) separating the second solution comprising lactic acid and monovalent lactate salt into lactic acid and a solution comprising the monovalent lactate salt by vapour-liquid separation;
g) recycling the solution of step f) comprising the monovalent lactate salt to step d).

Carrying out the water-splitting electrodialysis to a partial conversion of 40 to 98 mole % and subsequently recycling the remaining lactate salt to the electrodialysis step advantageously results in an optimal process with low power consumption and no substantial yield loss.

Furthermore, the process as described herein produces virtually no waste by-products, since all compounds formed and separated in the different steps may be recycled. The magnesium base separated in step c) may for instance be used in the fermentation process and the solution comprising monovalent base of step e) may be used in the salt exchange step b). The separation step f) also contributes to minimise the amount of non-reusable components since it does not generate further waste by-products.

The aqueous medium comprising a magnesium lactate salt may preferably be provided by a fermentation process. The magnesium lactate salt is generally already present in an aqueous medium when it leaves the fermentation. In such a process, a carbohydrate source is fermented to lactic acid by means of a lactic acid-producing micro-organism. During fermentation, a magnesium base is added as neutralising agent. This results in the formation of an aqueous medium comprising the corresponding magnesium lactate salt.

The base anion of the magnesium base is preferably chosen from at least one of hydroxide, carbonate and hydrogencarbonate, and more preferably is hydroxide. Although the use of magnesium as the base cation is preferred, another alkaline earth metal cation, such as a calcium cation, may also be used. The amount of alkaline earth metal base added is determined by the amount of lactic acid produced and may be determined via pH control of the fermentation medium.

The biomass (i.e. microbial cell matter) may be removed from the fermentation broth before further processing of the lactate-containing medium. Biomass removal may be effected, for example, by conventional methods including filtration, flotation, sedimentation, centrifugation, flocculation and combinations thereof. It is within the scope of the skilled person to determine an appropriate method. Other optional treatments prior to further processing include washing, filtration, (re)crystallisation, concentration and combinations thereof.

Magnesium is a preferred alkaline earth metal, since the use of a magnesium base advantageously results in the formation of magnesium lactate in an appropriate crystalline form to enable separation of the crystalline material from the fermentation broth including the biomass. Separation of the magnesium lactate may be done by any known processing technique for solid/liquid separations. It may be done for instance via filtration using a filter with a suitable pore size to retain magnesium lactate on the filter and to enable subsequent removal of impurities by washing of the filter cake. The above-mentioned biomass separation is in principle not needed unless there is the wish to further process or (re-)use the remaining fermentation broth for specific purposes.

The thus purified magnesium lactate is especially suitable for further processing as described herein and in particular when using water-splitting electrodialysis, wherein fermentation-derived products (e.g. sugar, protein, amino acids) may negatively interfere by, for instance, increasing the power consumption and fouling of the ion-permeable membranes.

The aqueous medium comprising the alkaline earth metal lactate salt, preferably the magnesium lactate salt, is subjected to a salt exchange reaction (step b), wherein a monovalent base is added to said aqueous medium to form a monovalent lactate salt and a solid alkaline earth metal base.

See also WO 2005/123647, which is incorporated herein by reference, describing the use of a magnesium base in lactic acid fermentation and the salt exchange reaction between magnesium lactate and a monovalent base.

If the aqueous medium containing the alkaline earth metal lactate is provided by fermentation, the base anion is generally chosen to correspond to the base anion used as neutralising agent during fermentation.

The monovalent base added is preferably a hydroxide, carbonate and/or hydrogencarbonate, more preferably a hydroxide, of a monovalent cation, the monovalent cation being sodium, potassium, lithium, ammonium, monoalkylammonium, dialkylammonium, trialkylammonium, or tetraalkylammonium, preferably sodium or potassium and more preferably sodium. The use of sodium and potassium bases advantageously results in a higher conversion of the alkaline metal earth lactate salt to the monovalent lactate salt than when ammonium um bases are used. This is relevant for preparing a product with a low alkaline earth metal ion content suitable for water-splitting electrodialysis. The residual alkaline earth metal ions may nonetheless be removed by methods known to the skilled person, such as the use of ion exchange resins.

The amount of monovalent base is determined by stoichiometric and pH considerations. It may be preferred to use a surplus of base to obtain a high conversion and to ensure the removal of virtually all alkaline earth metal ions from the lactate. In general, it is preferred to perform the salt exchange reaction in two steps, wherein in the first step the pH is between 9 and 12, preferably between 9.5 and 11, and in the second step the pH is slightly increased to a pH between 10.5 and 12.

The alkaline earth metal base formed in the salt exchange reaction typically is in solid form while the monovalent lactate salt is dissolved in the aqueous medium. The two components may therefore be separated by conventional solid-liquid separation processes, such as filtration and/or sedimentation.

The alkaline earth metal base obtained after separation may be recycled to the fermentation process.

Additional treatments, such as ion exchange treatment, activated carbon treatment, desalting electrodialysis, dilution, concentration and/or filtration (e.g. nanofiltration) may be performed prior to water-splitting electrodialysis. For instance, as a safety measure to prevent a too high alkaline earth metal level in the aqueous medium comprising the monovalent lactate salt, an ion exchange step may be performed prior to electrodialysis to lower the alkaline earth metal content thereof.

However, the process as described herein advantageously does not necessitate such additional treatments, especially when the lactate is provided via fermentation and a magnesium base is added in the fermentation process to provide magnesium lactate fermentation broth. In particular, the use of a magnesium base for neutralization during fermentation, which as discussed above provides magnesium lactate in an appropriate crystalline form, has been found to preclude the need of further purification steps generally required to remove the fermentation derived matter (e.g. sugar, protein and amino acid) from feeds for use in water-splitting electrodialysis. This advantageously lowers the complexity, power demand and costs generally associated to such electrodialytical processes.

The aqueous medium comprising the monovalent lactate salt is then subjected to water-splitting electrodialysis.

The initial concentration of the monovalent lactate salt in the aqueous medium that is subjected to electrodialysis (the feed solution) is between 10 and 30 wt. %. Preferably, the monovalent lactate salt concentration is between 20 and 25 wt. %. Depending on the salt concentration, the aqueous medium comprising the monovalent lactate salt as obtained after the salt exchange reaction, i.e. after the separation step c), may be used directly as feed to the electrodialysis, or, if necessary, may be diluted or concentrated to adjust the salt concentration prior to water-splitting electrodialysis. Concentration may be carried out by for instance evaporation or conventional electrodialysis.

The concentration of the monovalent lactate salt in the aqueous medium may be determined by methods known to the skilled person, for instance by using conductivity measurements and Inductively Coupled Plasma mass spectrometry analysis.

The water-splitting electrodialysis is carried out to a partial conversion of 40 to 98 mole %. Preferably, the electrodialysis is carried out to a partial conversion of 40 to 95 mole %, more preferably of 50 to 95 mole %, even more preferably of 60 to 95 mole %, even more preferably of 70 to 90 mole %, even more preferably of 80 to 90 mole %, and most preferably of about 85 mole %. A first solution comprising monovalent base and a second solution comprising lactic acid and monovalent lactate salt are produced in this process.

A partial conversion of 40 to 98 mole % means that 40 to 98 mole % of the monovalent lactate salt present in the feed solution is converted into lactic acid. This results in the second solution produced by the electrodialysis comprising lactic acid in an amount of 40 to 98 mole %, calculated on the total molar amount of lactic acid and lactate present in the solution.

The degree of conversion may be monitored by measuring conductivity of the second solution using methods known to the person skilled in the art.

In addition to the conversion level and the initial salt concentration of the feed solution, the conductivity of the second solution will depend on the temperature of the electrodialysis process. The higher the temperature at which the electrodialysis is performed, the lower the power consumption will be. Hence, the working temperature is chosen to optimise power consumption without compromising the performance and the life of the ion-specific permeable membranes. Generally, the water-splitting electrodialysis is performed at a temperature between 25° C. and 40° C. However, it is preferred to conduct the electrodialysis at a temperature higher than 50° C., for instance between 60° C. and 80° C., to allow for a low power consumption and the possibility for heat recovery.

The water-splitting electrodialysis as described herein may be performed using a conventional apparatus and conventional methods. Preferably the water-splitting electrodialysis is carried out in an electrodialysis apparatus provided with a cation exchange membrane and a bipolar membrane. A typical water-splitting electrodialysis cell comprises a two compartment unit. The aqueous medium comprising the monovalent lactate salt is introduced in the salt/acid compartment (or feed compartment). The monovalent cations are transported from the salt/acid compartment to the base compartment through the cation exchange membrane to produce the first solution comprising the monovalent base. Simultaneously, $H^+$ ions are transported to the salt/acid compartment to produce the second solution comprising lactic acid and monovalent lactate salt.

It is preferred to apply the water-splitting electrodialysis to monovalent lactate salts of sodium and potassium. When using ammonium lactate, care must be taken to control the emission of toxic ammonia resulting from the generation of ammonium hydroxide.

The second solution produced by the water-splitting electrodialysis is separated into lactic acid and a solution comprising the monovalent lactate salt. The separation may be achieved by vapour-liquid separation, liquid-liquid separation and/or solid-liquid separation.

The lactic acid is preferably separated from the monovalent lactate salt by means of vapour-liquid separation. Vapour-liquid separation may be performed by distillation or evaporation. Distillation is preferred, since it provides a substantially complete separation of the acid from the salt. The solution comprising lactic acid and monovalent lactate salt may be concentrated prior to distillation. Distillation is preferably carried out in a vacuum distillation unit. Vacuum distillation is found to be especially suited to separate lactic acid from lactate salt in a situation where the mixture of lactic acid and lactate salt is obtained by water-splitting electrodialysis being carried out to a partial conversion as described herein and where magnesium base is used for neutralisation in fermentation.

A suitable process and/or apparatus for concentration and vacuum distillation is described in WO 01/38283, which is incorporated herein by reference. The distillation process may comprise two or more distillation steps, the first distillation step preferably being carried out at a temperature from 80 to 150° C., preferably from 100 to 140° C., and a pressure between 50 and 250 mbar, preferably between 60 and 150 mbar, and the second distillation step preferably being carried out at a temperature from 80 to 200° C., preferably from 100 to 200° C., and a pressure between 0.01 and 50 mbar, preferably between 0.1 and 20 mbar.

The first distillation step may comprise a combination of one or more film evaporators with distillation columns and serves the purpose of concentrating the lactic acid/sodium lactate product stream as high as possible.

The second distillation step may also comprise a combination of one or more film evaporators with one or more distillation units. In the second distillation step, the majority of the lactic acid in the product of the first distillation step is distilled, preferably under vacuum, forming a top fraction comprising the majority of the lactic acid and a distillation residue (bottom fraction) comprising the sodium lactate. The second distillation step may be carried out in one or more short path distillation (SPD) devices having an inner condenser. However, in order to reduce contamination by splashing of impurities into the condensed lactic acid, i.e. to minimise the sodium content in the distilled lactic acid product, the use of a vacuum distillation unit as described in FIGS. 5A and 5B of the above-mentioned WO 01/38283 (see page 10, line 17, to page 11, line 7) is preferred, as this specific set up prevents any splashing from taking place. Preferably, the second distillation step comprises a film evaporator (preferably a falling film, a wiped film or a thin film evaporator) that is at the bottom of the evaporator directly in connection with—or is connected via a specifically U-shaped connection with—a vacuum distillation unit comprising a packing and preferably a cooling device so that it may be operated under reflux. In the film evaporator, the lactic acid is brought in vapour phase after which it enters the vacuum distillation through the connection at the bottom where it subsequently is distilled.

It is further preferred for the product from the first distillation step (the first bottom fraction) to be subjected to a conditioning step (so-called "preflash") before it undergoes a second distillation step, the pressure in this conditioning step preferably being the same as that used in the second distillation. This preferred embodiment has the advantage that a residual quantity of water and dissolved gases are removed before the product is subjected to the second distillation step. The use of a preflash allows the lactic acid/sodium lactate content to be increased so that in the second distillation step it is possible to obtain both a purer lactic acid product and to achieve more stable operation.

Liquid-liquid separation may comprise extraction, and, for the recovery of lactic acid from the loaded solvent, back extraction, or other techniques. Liquid-liquid separation may also comprise filtration, e.g., ultrafiltration, microfiltration, nanofiltration, reverse osmosis or decantation.

Solid-liquid separation may comprise a crystallisation step. For example, the lactic acid may be crystallised in a static crystallisation unit, by fractional crystallisation, by suspension crystallisation and/or by wash column crystallisation. The crystals may then be separated from the liquid phase of the solution crystals by filtration or centrifugation. The crystallisation may comprise a concentration step, such as a water evaporation step, a cooling step and/or a seeding step and one or more washing steps. Solid-liquid separation, and in particular crystallisation, has the disadvantage that, in order to ensure a product of high purity, the yields of recovery are generally low. For instance, in some processes after a first crystallisation the yield of recovery of lactic acid is about 46% and the purification factor is 15-20, which is the ratio of the amount of impurities in the product before and after crystallisation. To achieve a purification factor of between 100-160, a second crystallisation step is required and the overall yield then drops to 22%.

The solution containing the monovalent lactate salt obtained after separation, typically containing at least 5 wt. % lactate salt, preferably at least 30 wt. % lactate salt based on the total weight of lactic acid and lactate, is recycled to the water-splitting electrodialysis. This recycling step ensures that no substantial yield loss is suffered as a consequence of the partial conversion of the lactate into lactic acid during water-splitting electrodialysis.

The lactic acid product obtained after the separation step f) may be in solid form, liquid form or in solution, and generally comprises at least 95 wt. % of lactic acid, preferably at least 97 wt. % of lactic acid, more preferably at least 99 wt. % of lactic acid, even more preferably at least 99.5 wt. % of lactic acid and most preferably at least 99.9 wt. % of lactic acid. The lactic acid obtained by the process according to an aspect of the invention is therefore of high purity and is suitable for direct use in, for example, synthetic processes, food applications and cosmetic applications.

The lactic acid obtained is especially suited for the preparation of lactide and/or polylactic acid, wherein during the polymerisation of lactic acid the presence of impurities, such as lactate salts, may result in undesirable racemisation of lactic acid moieties leading to a lactide and polylactic acid product of lower quality. In general the amount of metal ions should be below 5 ppm. For instance, the presence of sodium sulfide, in quantities as low as 20 ppm, in lactic acid negatively affects the optical purity of the polylactic acid product (Example 1).

Any conventional process as known to the person skilled in the art may be used for said manufacture of lactide and/or polylactic acid provided that the starting material containing lactic acid is made via the process as described herein.

The process as described herein advantageously is accompanied by a low power consumption and ensures that no or substantially no waste by-products are generated.

Aspects of the present invention are further illustrated by the following Examples, without being limited thereto or thereby.

EXAMPLE 1

Partial Electrodialysis of Sodium Lactate Solution

An Electrocell electrodialysis module (Sweden) was equipped with a Fumatech FBM bipolar membrane, and a Neosepta CMB cation exchange membrane. A set-up with two electrode compartment and one feed compartment was used. The membrane areas of the bipolar and the cation exchange membrane was 0.01 m$^2$. The first compartment comprised of the anode and the cation exchange side of the bipolar membrane, the second feed compartment of the anion exchange side of the bipolar membrane and the cation exchange membrane, and the third compartment of the cation exchange membrane and the cathode. 2 wt. % sulphuric acid in water was circulated through the anode compartment to ensure a high conductivity. A 20 wt. % sodium lactate solution was circulated through the middle compartment as a feed. A 8 wt. % sodium hydroxide solution was circulated through the cathode compartment to ensure a high conductivity at the cathode side, and to collect the sodium hydroxide produced. The three solutions were circulated with a peristaltic pump at 250 ml/min from a 500 ml glass buffer over the electrodialysis module. The glass buffer vessel were double walled and the temperature across the three compartments was kept between 40 and 60° C. with a water bath. The sulphuric acid, sodium hydroxide were reagent grade, and the Purac sodium lactate was of high purity food grade quality.

The electrodialysis experiment was carried out a constant 7.5 A DC current. In the experiment the sodium lactate solution in the feed compartment of the module was acidified batch wise through sodium removal through the cation exchange membrane to form sodium hydroxide in the cathode compartment, while protons generated by the bipolar membrane formed lactic acid with the original lactate ions.

The experiment lasted for about 230 min, when all lactate was converted. In the beginning of the experiment the sodium lactate solution had a high conductivity and the voltage was relatively constant at 9.5 to 10.5 V. After 180 min 80% of the sodium lactate was converted to lactic acid, with a residual sodium content of 0.84 wt. %, and the voltage increased to 12 V. The pH of the solution decreased to 3.1 from an initial pH of 6.0. After 210 min the conversion had increased to 94%, the residual sodium content had decreased to 0.25 wt. %, the voltage had increased to 16 V, and the pH had decreased to 2.56. After 225 min the conversion had increased to 98%, the residual sodium content had decreased to 0.06 wt. %, the voltage had increased to 22.4 V, and the pH had decreased to 2.56. The rapid voltage increase in these time intervals is the consequence of the progressively lower conductivities of the feed solution. This voltage increase results in a rapid increase in power consumption to convert residual sodium lactate. These results indicate that an economical process is only obtained by carrying out the electrodialysis to a partial conversion of at the most 98%.

In the time interval of 180-210 minutes the current efficiency, calculated with the theoretical mass flows based on the current and Faradays law, and the actual mass flows based on analytical data of lactate, lactic acid and sodium was 0.68. In the time interval of 210-225 the current efficiency dropped to 0.64, and at conversions higher than 98% the current efficiency dropped to 0.36 or below. This means that at higher conversions the energy input itself increases but it also means that increasingly less of the electrical energy consumed is used for conversion.

EXAMPLE 2

Distillation of Lactic Acid From a Solution of Lactic Acid and Sodium Lactate

A solution of lactic acid and sodium lactate was prepared by adding 98.4 grams of a 60 wt. % food grade sodium lactate solution to 4310 grams of a 49 wt. % food grade lactic acid solution. This solution is representative of a mixture of lactic acid and sodium lactate that is obtained after electrodialysis with partial conversion and that is concentrated by evaporation of water. A glass lab Short Path Distillation (SPD) unit was used to concentrate this solution further, and subsequently distil lactic acid from it.

The lab SPD unit used was a glass KDL4 type unit, made by UIC. The SPD unit is essentially a double walled column, which can be heated with an oil bath to temperatures to above 100° C. The liquid (i.e. the lactate/lactic acid feed solution) may be fed to the top of the SPD unit by pumping it with a peristaltic pump. The SPD unit is equipped with a top stirrer and wipers in such a way that a liquid film may be produced on the inner wall of the SPD unit column from the liquid that is pumped in from the top. The top of the SPD unit is also connected to a vacuum system, comprising a glass column, which is indirectly cooled through a double wall by a cold finger at −60° C., an oil operated vacuum pump and a pressure control unit with a vacuum meter and a pressure valve. By applying vacuum and high temperature a relatively high boiling compound like lactic acid can be evaporated from the feed. The evaporated lactic acid can then be condensed in the SPD unit, which is equipped with an inner condenser cooled by water at 55° C. The lactic acid can be collected in a glass bulb placed directly under the inner condenser of the SPD unit. The part of the feed that is not evaporated can be collected using an outlet on the side wall at the bottom of the double walled SPD column. Vapours that are not trapped on the inner condenser of the SPD unit are trapped in the glass column in the vacuum section operated with the cold finger.

First the feed solution was led over the SPD unit for dewatering. The oil temperature was 120° C., the vacuum pressure 100 mbar, and the feed rate 10 ml/min. The inner condenser of the SPD unit was operated with tap water. A fraction of 336 g of a dewatered mixture of lactic acid and sodium lactate was collected, and immediately passed over the SPD unit again. Now the oil temperature was 130° C., the vacuum pressure 6 mbar, the feed flow rate was 15 ml/min, and the inner condenser of the SPD unit was cooled to 55° C. In this second SPD step at least half of the feed was distilled and recovered as a purified lactic acid, the overall recovery yield of lactic acid being of 65% (based on the total weight of lactic acid present in the original feed). The feed to the SPD unit in this second step contained 5500-6000 ppm sodium, while the lactic acid product contained only 112 ppm sodium, i.e. a purification factor of about 49-54. Thus, the bulk of the lactic acid can be recovered in a pure form from the original mixture of lactic acid and sodium lactate using a short path distillation (SPD) unit.

The invention claimed is:

1. A process for the preparation of lactic acid comprising the:
   a) providing an aqueous medium comprising magnesium lactate;
   b) adding to the aqueous medium comprising magnesium lactate a monovalent base to form an aqueous medium comprising a water soluble monovalent lactate salt and a solid magnesium base;
   c) separating the magnesium base from the aqueous medium comprising the water soluble monovalent lactate salt;
   d) adjusting the concentration of the monovalent lactate salt in the aqueous medium to a value between 10 and 30 wt. %,
   e) subjecting the aqueous medium comprising the monovalent lactate salt to water-splitting electrodialysis, to produce a first solution comprising monovalent base and a second solution comprising lactic acid and monovalent lactate salt, the electrodialysis being carried out to a partial conversion of 40 to 98 mole %;
   f) separating the second solution comprising lactic acid and monovalent lactate salt into lactic acid and a solution comprising the monovalent lactate salt by vapour-liquid separation;
   g) recycling the solution of step f) comprising the monovalent lactate salt to step d).

2. The process according to claim 1, wherein the vapour-liquid separation comprises distillation.

3. The process according to claim 1, wherein the electrodialysis is carried out to a partial conversion of 40 to 95 mole %.

4. The process according to claim 3, wherein the electrodialysis is carried out to a partial conversion of about 85 mole %.

5. The process according to claim 1, wherein concentration of the monovalent lactate salt in the aqueous medium of d) is adjusted to a value between 20 and 25 wt. %.

6. The process according to claim 1, wherein the first solution comprising the monovalent base produced by the water-splitting electrodialysis of step e) is recycled to step b).

7. The process according to claim 1, wherein the water-splitting electrodialysis is carried out in an electrodialysis apparatus provided with a cation exchange membrane and a bipolar membrane.

8. The process according to claim 1, wherein the aqueous medium comprising the magnesium lactate is provided by fermentation, wherein a carbohydrate source is fermented by means of a micro-organism to form lactic acid, a magnesium base being added as neutralising agent during fermentation to provide the magnesium lactate.

9. The process according to claim 8, wherein the magnesium base is magnesium hydroxide.

10. The process according to claim 8, wherein the aqueous medium comprising the magnesium lactate is subjected to a separation step to remove microbial cell matter prior to step b).

11. The process according to claim 1, wherein the monovalent base in step b) comprises a cation that is a sodium, potassium, lithium, ammonium, monoalkylammonium, dialkylammonium, trialkylammonium or tetraalkylammonium cation.

12. The process according to claim 1, wherein the lactic acid obtained after the separation step f) comprises at least 95 wt. % of lactic acid.

13. A process for the preparation of lactide and/or polylactic acid, comprising preparing lactic acid using the process according to claim 1 and reacting the lactic acid to form lactide and/or polylactic acid.

14. The process according to claim 1, wherein the vapour-liquid separation comprises distillation carried out in a vacuum distillation unit.

15. The process according to claim 1, wherein the electrodialysis is carried out to a partial conversion of 50 to 95 mole %.

16. The process according to claim 1, wherein the electrodialysis is carried out to a partial conversion of 60 to 95 mole %.

17. The process according to claim 1, wherein the electrodialysis is carried out to a partial conversion of 80 to 90 mole %.

18. The process according to claim 1, wherein the monovalent base in step b) comprises a cation that is a sodium or potassium cation.

19. The process according to claim 1, wherein the monovalent base in step b) comprises a cation that is a sodium cation.

20. The process according to claim 1, wherein the lactic acid obtained after the separation step f) comprises at least 97 wt. % of lactic acid.

21. The process according to claim 1, wherein the lactic acid obtained after the separation step f) comprises at least 99 wt. % of lactic acid.

22. The process according to claim 1, wherein the lactic acid obtained after the separation step f) comprises at least 99.5 wt. % of lactic acid.

23. The process according to claim 1, wherein the lactic acid obtained after the separation step f) comprises at least 99.9 wt. % of lactic acid.

* * * * *

UNITED STATES PATENT AND TRADEMARK OFFICE
CERTIFICATE OF CORRECTION

PATENT NO. : 8,772,440 B2  
APPLICATION NO. : 13/577398  
DATED : July 8, 2014  
INVENTOR(S) : Peter Johannes Marie Baets and Willem Jacob Groot Page 1 of 1

It is certified that error appears in the above-identified patent and that said Letters Patent is hereby corrected as shown below:

In the Claims,

In column 9:

In Claim 1, line 34, delete "the".

Signed and Sealed this  
Twelfth Day of May, 2015

Michelle K. Lee  
*Director of the United States Patent and Trademark Office*